(12) United States Patent
Tozzi et al.

(10) Patent No.: US 8,439,979 B2
(45) Date of Patent: May 14, 2013

(54) ARTIFICIAL CONTRACTILE STRUCTURE AND APPARATUS COMPRISING SUCH STRUCTURE

(75) Inventors: Piergiorgio Tozzi, Lausanne (IT); Daniel Hayoz, Villars-sur-Glâne (CH); Ludwig Von Segesser, Lausanne (CH); Enzo Borghi, Budrio (IT); Martin Horst, Horw (DE)

(73) Assignee: MyoPowers Medical Technologies SA, Lausanne (CH)

( * ) Notice: Subject to any disclaimer, the term of this patent is extended or adjusted under 35 U.S.C. 154(b) by 235 days.

(21) Appl. No.: 12/667,645

(22) PCT Filed: Jul. 4, 2008

(86) PCT No.: PCT/EP2008/058730
§ 371 (c)(1),
(2), (4) Date: Mar. 23, 2010

(87) PCT Pub. No.: WO2009/004092
PCT Pub. Date: Jan. 8, 2009

(65) Prior Publication Data
US 2010/0204803 A1 Aug. 12, 2010

(30) Foreign Application Priority Data

Jul. 4, 2007 (WO) .................. PCT/IB2007/052620
Feb. 19, 2008 (EP) ...................................... 08101738

(51) Int. Cl.
*A61F 2/04* (2006.01)
*A61F 2/00* (2006.01)
*A61B 17/08* (2006.01)

(52) U.S. Cl.
USPC ........................... 623/23.65; 600/37; 606/157

(58) Field of Classification Search .............. 600/30–31, 600/37; 623/23.64–23.76; 606/157
See application file for complete search history.

(56) References Cited

U.S. PATENT DOCUMENTS 6,080,194 A * 6/2000 Pachence et al. .......... 623/23.76
6,261,222 B1 * 7/2001 Schweich et al. ............... 600/16
(Continued)

FOREIGN PATENT DOCUMENTS

EP 1 238 638 9/2002
EP 1 968 482 6/2009
(Continued)

OTHER PUBLICATIONS

Toki Corporation: "BioMetal Fiber", Internet Citation, [Online] pp. 1-2, XP002490131, Retrieved from the Internet http://www.toki.co.jp/BioMetal/Download/DownLoadFiles/BMF_eng.pdf [retrieved on Jul. 29, 2008] abstract.

(Continued)

*Primary Examiner* — Suzette J Gherbi
(74) *Attorney, Agent, or Firm* — Young & Thompson

(57) ABSTRACT

An artificial contractile structure generally devised to be used in the medical field to assist the functioning of an organ, includes a support (2) and one or more fibers (5) fixed thereto. The fibers are made of a contractile material which can be activated by an activator so as to provide the structure in a rest or activated position, the activated position being defined with fibers of reduced length compared to their length in the rest position. The structure is adapted to be placed around a hollow part of an organ to be contracted. The fibers are distributed along the support in order to be able to reduce the volume of the hollow part, when the fibers are contracted. The fibers and the activator are designed so that the temperature of fluids or tissues surrounding the organ does not increase above 40° C., preferably 39° C., and more preferably 38° C.

36 Claims, 6 Drawing Sheets

U.S. PATENT DOCUMENTS

| | | | |
|---|---|---|---|
| 7,233,097 B2 | 6/2007 | Rosenthal et al. | |
| 7,407,479 B2 * | 8/2008 | Forsell | 600/29 |
| 7,695,427 B2 * | 4/2010 | Kugler et al. | 600/37 |
| 8,080,022 B2 * | 12/2011 | Deem et al. | 606/151 |
| 2004/0143343 A1 * | 7/2004 | Grocela | 623/23.66 |
| 2005/0020871 A1 | 1/2005 | Tozzi et al. | |
| 2005/0256367 A1 * | 11/2005 | Banik | 600/30 |
| 2006/0047180 A1 * | 3/2006 | Hegde et al. | 600/30 |
| 2006/0161041 A1 * | 7/2006 | Forsell | 600/30 |
| 2006/0287571 A1 * | 12/2006 | Gozzi et al. | 600/30 |
| 2007/0043256 A1 * | 2/2007 | Banik | 600/31 |
| 2008/0021260 A1 * | 1/2008 | Criscione et al. | 600/16 |
| 2008/0200965 A1 * | 8/2008 | Forsell | 607/41 |
| 2009/0240100 A1 * | 9/2009 | Forsell | 600/30 |
| 2010/0145138 A1 * | 6/2010 | Forsell | 600/30 |
| 2011/0066254 A1 * | 3/2011 | Forsell | 623/23.64 |
| 2011/0087337 A1 * | 4/2011 | Forsell | 623/23.68 |
| 2011/0124954 A1 * | 5/2011 | Ogdahl et al. | 600/30 |

FOREIGN PATENT DOCUMENTS

| | | |
|---|---|---|
| JP | 7-51304 | 2/1995 |
| WO | 2006/121818 | 11/2006 |
| WO | 2007/077513 | 7/2007 |

OTHER PUBLICATIONS

John B. Blottman, "Engineering Acoustics, Underwater Acoustics, and ECUA: Sonar Transducer Design and Modeling I", J. Acoust. Soc. Am., vol. 123, No. 5, Pt. 2, May 2009, pp. 3013-3014.

International Search Report dated Nov. 13, 2008, from corresponding PCT application.

H. Emoto et al., "Systemic and local effects of heat dissipation in the thermally powered LVAS", Department of Artificial Organs, Cleveland Clinic Foundation, OH 44106, ASAIO Trans. Jul.-Sep. 1988; 34(3):361-6, pp. 1.

* cited by examiner

ARTIFICIAL CONTRACTILE STRUCTURE AND APPARATUS COMPRISING SUCH STRUCTURE

TECHNICAL FIELD

The present invention relates to artificial contractile structures generally devised to be used in the medical field. Such structures may be advantageously used to assist the functioning of an organ, e.g. a sphincter or the heart. More generally, they can be used for moving a hollow or a tubular part of the body. The present invention relates also to an apparatus comprising such structure.

The present application incorporate by reference the complete teaching of international patent application PCT/IB2006/055044 filed by the same applicant.

BACKGROUND OF THE INVENTION

It is known to use artificial structures to assist muscular contraction. Such structures are adapted to assist atrial or ventricular contraction, or to assist or replace a natural sphincter. The use of such artificial sphincters increases currently because the faecal and urinary incontinences affect now 10% of people over 60 years of age and dramatically increase over 80. Several pharmaceutical or surgical solutions have been developed for treating incontinence. Generally, the outcome of surgery for treatment of urinary and faecal incontinence has to be regarded as low. The impacts on health care costs and overall quality of life of the patient are enormous.

The AMS800 artificial sphincter for urinary incontinence is commercialized by American Medical Science and is composed of three components, a cuff, a pump, and a pressure-regulating balloon. The cuff is implanted at the bulbous urethra in males and is inflatable by means of a fluid. The pump is implanted in the scrotum and the pressure-regulating balloon is implanted in the abdomen. The major problems when using AMS800 is the tissue erosion around the urethra due to the constant pressure, the atrophy and irritation of tissues at the location of the inflatable cuff, and the emergency surgery for repair as the device stays in close position in the event of mechanical failure. All commercialized artificial sphincters whether for urinary or feacal incontinence bear the same drawbacks.

The ProAct artificial sphincter for urinary incontinence is commercialized by Uromedica and is composed of two small implantable balloons. During a short outpatient procedure, the balloons are surgically placed under the skin in the area where the prostate of the patient was surgically treated. The balloons help protect against accidental leaking of urine by increasing the amount of pressure required to urinate. When the patient need to urinate, a normal amount of effort still should be required to push the urine out. However, the pressure from the balloons will help guard against unintentional urine loss, such as during a sneeze or cough. The major problems when using ProACT are identical to the problems using AMS800 artificial sphincter described above.

Some publications describe the use of artificial sphincters comprising shape memory alloy elements suitable for opening and closing a part of an organ in a living body. EP 1 238 638 describes an artificial sphincter having an opening/closing portion for opening and closing, wherein said opening/closing portion has:
 a pair of elongated shape memory alloy elements that change reversibly between opposite shapes upon changes in temperature, and
 hinges that link said pair of shape memory alloy element together in a cylindrical shape.

Such artificial sphincter is placed around the intestine of a human or animal inside the body near to an intestinal opening so that the opening/closing portion constricts the intestine. When the shape memory alloy elements are heated, they change shape, so that the constricting force on the intestine is lost.

However, as the opening/closing portion is still constricting the same region of the intestine, there is a damage to this part of the body, and more especially a risk of tissue erosion, atrophy and burns, due to the constant pressure and heating of the shape memory alloy elements.

Reversible thermal lesions occur when the local temperature is increased to the 42° C. to 44° C. range (5 C-7° C. over the normal body temperature of 37° C.) and that irreversible thermal lesions occur when the local temperature is increased above 45° C. (>8° C. temperature rise over normal).

Moreover, in normal state, the shape memory alloy elements are not heated and are each bent to constrict the intestine. That means that heating is necessary to open the artificial sphincter. If the heating means fail, the sphincter remains closed and cannot be open what may be leading to life threatening complications. A surgery is then necessary to open the artificial sphincter and solve the problem.

Another artificial sphincter has been proposed in JP 07-051304. This document describes a constrictor comprising two shape memory alloy elements with different shape memories, and covered by covering materials. The first covering material is formed in a shape to close the urethra in the daytime, and the second covering material is formed in a shape to half closed the urethra in the night. This sphincter allows to change the pressure to the urethra, in order to prevent the incontinence in life action in the daytime, and to avoid necrosis of the tissue by loosing the pressure to the urethra in the night.

However, the drawbacks of such artificial sphincter are that there is a risk of necrosis and consequential tissue erosion, due to the constant pressure to the urethra during the day and that there is a risk of incontinence during the night.

Therefore there are, at the present time, no adequate solutions, whether commercial or in the literature, for implanting artificial contractile structures, particularly for the treatment of faecal or urinary incontinence.

SUMMARY OF THE INVENTION

The present invention provides an artificial contractile structure which allows to avoid the disadvantages of the prior art.

Accordingly, the present invention relates to an artificial contractile structure comprising a support and one or more fibers fixed to said support, said fibers being made of a contractile material which can be activated by an activator in such a way as to provide said structure in a rest or in an activated position, the activated position being defined with fibers of reduced length compared to their length in rest position, said structure being adapted to be placed around a hollow part of an organ to be contracted, wherein the fibers are distributed along said support in order to be able to reduce the volume of said hollow part, when said fibers are contracted, wherein the fibers are designed in such a way that the temperature of fluids or tissues surrounding said organ does not increase above 40° C., preferably 39° C., and more preferably 38° C.

It has been found that the control of temperature is a significant parameter for avoiding tissue necrosis and tissue erosion, and surprisingly that less than 3° C., preferably less than 2° C., and more preferably less than 1° C., over the normal human body temperature (of 37° C.), is particularly protective of the tissue surrounding, and this irrespective of the shape and nature of the contractile-powered structure. This is particularly surprising as a temperature increase of 7° C. to 8° C. over the normal body temperature of 37° C. is not known to create tissue lesions (Hemoto H et al. Systemic and local effects of heat dissipation in the thermally powered LVAS. ASAIO trans. 1988 July-September; 34(3):316-6).

Advantageously, the present invention provides an artificial contractile structure and an apparatus comprising such structure which are designed for chronic applications (i.e. long-term implantation), for example for many months and preferably many years.

In some embodiments, the length, the diameter and the shape of the fibers are selected in such a way that the average power to supply to the activator is able to be less than 3 W, preferably less than 1 W, more preferably less than 0.5 W.

In another embodiments, the fibers may be designed to be activated by an activator or controller which can comprise a microprocessor designed to generate micropulses having a duration lower than 100 ms, preferably comprised between 5 ms and 50 ms, more preferably between 10 ms and 20 ms and a power, which progressively increases, until the required length of the fibers is achieved. This power generation is optimally designed to avoid a constant overheating of the fibers, which could damage the fibers and create tissue lesions.

In other embodiments, the fibers are distributed along said support in order to be able to reduce the volume of said hollow part, when said fibers are contracted, in at least two distinct regions of the hollow part, and wherein the fibers are designed to be activated pulsatory and alternately, so as to allow one or more contraction points along at least one of said regions of said hollow part, in a pulsating and alternating manner relating to one or more other contraction points operated by the fibers along the other region of said hollow part.

The fibers may be activated in such a way that the strength of the contractions applied to a region is substantially the same as the strength of the contractions applied to another region.

In another aspect, strength of the closing of the tubular part may be adjusted to the particular body fluids with the objective to minimize or suppress leaking. Preferably, the activated fibers are designed to apply, in a pulsating and alternating manner, a pressure on an organ to be contracted, which is comprised between 10 g/cm$^2$ and 200 g/cm$^2$, during a period comprised between 30 seconds to 30 minutes, preferably between 30 seconds to 10 minutes, and more preferably between 1 minute to 5 minutes. Preferably, the strength is such that the regions are completely closed in a pulsating and alternating manner.

In a preferred embodiment, the structure is adapted to be placed around a tubular part of an organ to be contracted and the fibers are distributed in such a way that they are able to reduce the diameter of said tubular part, when said fibers are contracted, in at least two distinct regions of the tubular part, the fibers being designed to be activated pulsatory and alternately, so as to close at least one region of the tubular part, in a pulsating and alternating manner relating to the other region.

Such artificial structure may be used in several indications, e.g. for assisting or replacing a natural sphincter, especially for the treatment of faecal or urinary incontinence, for assisting atrial or ventricular contraction, for assisting the respiratory function, for assisting or replacing a paralyzed muscle or for treating venous insufficiency. The present invention is particularly designed for improving sphincter muscle function and therefore to improve the patient's quality of life with a significant reduction of treatment costs.

In some embodiments, the fibers have at least two distinct parts fixed to the support.

In some embodiments, the transition from the rest towards the activated position or vice-versa is defined by a fiber movement along a lateral direction which is perpendicular with respect to the fiber length.

In some embodiments, the fibers are fixed on a support that covers at least 20% of the surface of the tubular part where the structure is placed, preferably 50% of said surface, with at least two fibers forming a loop on the tubular part and connected to the support.

In a preferred embodiment, the support is a hinged clamp adapted to be placed around the tubular part, comprising at least two pairs of teeth, wherein one or more fibers are fixed to the inside of each pair of teeth in order to cross it so as to form at least two gates, each gate being able to constrict one region of the tubular part to close it, in a pulsating and alternating manner relating to the other gate.

In another embodiment, the support comprises parallel rods to which at least two fibers are fixed by their ends, so that each fiber or combination of fibers forms a loop adapted to be placed around the tubular part, the loops forming at least two gates, each gate being able to constrict one region of the tubular part to close it, in a pulsating and alternating manner.

In another embodiment, the support comprises a U rod to which at least two fibers are fixed by their central part, so that each fiber or combination of fibers forms a U adapted to be placed around the tubular part, the U fibers forming at least two gates, each gate being able to constrict one region of the tubular part to close it, in a pulsating and alternating manner.

In another embodiment, the support comprises a housing adapted to be placed around the tubular part, said housing being closed by a sliding element, and wherein at least two fibers are suspended by their ends to the support, the central part of each fiber comprising a press pad placed opposite the sliding element, the fibers and their press pads forming at least two gates, each gate being able to constrict one region of the tubular part to close it, in a pulsating and alternating manner.

In another embodiment, the support may have a form adapted to be placed around the hollow part of organ to be contracted, and wherein the fibers are designed to form at least two bundles, each bundle being suspended by their ends to said support and forming a loop around said hollow part, each bundle being able to contract one region of the hollow part, in a pulsating and alternating manner.

In another embodiment, the support may be divided in separable individual elements, each individual element comprising fibers distributed along said individual element in order to be able to reduce the volume of said hollow part, when said fibers are contracted, and the fibers of each individual element are designed to be activated pulsatory and alternately relating to the other individual elements. Said individual element may comprise assembly means for cooperating with complementary assembly means of another individual element.

In another aspect, the present invention provides an apparatus comprising an artificial contractile structure as described above, and further comprising an activator or controller linked to said structure and adapted to pulsatory and alternately contract the fibers as described above, said activator being designed in such a way that the temperature of fluids or tissues surrounding said organ does not increase above 40° C., preferably 39° C., and more preferably 38° C.

In a preferred embodiment of the apparatus, the activator or controller linked to the structure may be adapted to pulsatory and alternately contract the fibers so that said fibers close at least one region of the tubular part, in a pulsating and alternating manner relating to the other region, and the apparatus further comprises means for opening on demand said artificial contractile structure.

In some embodiments of the apparatus, the activator and the fibers are designed in such a way that the activated fibers apply a pressure on the region of the organ to be contracted, which is comprised between 10 g/cm$^2$ and 200 g/cm$^2$, during a period comprised between 30 seconds to 30 minutes, preferably between 30 seconds to 10 minutes, and more preferably between 1 minute to 5 minutes. Preferably, the regions may be completely closed in a pulsating and alternating manner.

In other embodiments, the apparatus may further comprise an implantable source of energy.

Advantageously, the apparatus is designed so that the required average power to supply by the source of energy is less than 3 W, preferably less than 1 W, more preferably less than 0.5 W.

The source of energy may be a commercial-available transcutaneously rechargeable battery. It may also be an electro-active polymer designed to create energy by transformation of mechanical contraction, for example in the shape of an elastomeric band that is fixed on moving structures, such as beating heart, chest or bone joint. The polymer may also be designed for an ultra-low power acoustic receiver.

In some embodiments, the activator may comprise a microprocessor designed to generate micropulses having a duration lower than 100 ms, preferably comprised between 5 ms and 50 ms, more preferably between 10 ms and 20 ms and a power, which progressively increases, until the required length of the fibers is achieved. Preferably, the microprocessor may be further designed to have a continuous feedback on the resistance of the fibers.

Advantageously, the apparatus may comprise no sensor and may comprise means designed to allow a self-monitoring of the apparatus.

In other embodiments, the apparatus may further comprise sensing means selected from pressure, temperature and movement sensing means. Said sensing means can be fixed to the support of the artificial contractile structure, may even form part of it, or may be separated from the support.

In some embodiments, the apparatus is a single device containing the artificial contractile structure, the controller and the implantable source of energy.

In a best-mode embodiment, the present invention provides an apparatus comprising an artificial contractile structure as described above, an activator or controller linked to said structure and adapted to pulsatory and alternately contract the fibers, an implantable source of energy, said apparatus being designed so that the required average power to supply by the source of energy is less than 3 W, preferably less than 1 W, more preferably less than 0.5 W.

The different features of the structure of apparatus described above may be used separately or together if appropriate.

DETAILED DESCRIPTION

Figure 1:
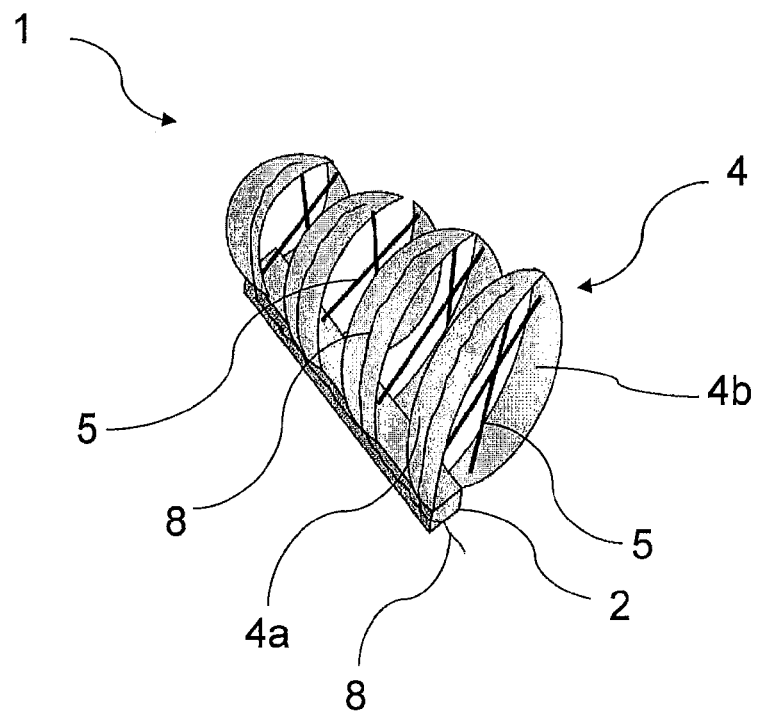
FIG. 1 is a side view of a first embodiment of the artificial structure according to the present invention.

In the present description, the terms "tubular part of an organ" means a region of a hollow organ in the living body having an overall cylindrical shape, for example a blood vessel, the urinary tract, the colon, the stomach or any other body part against which pressure can be applied. A "hollow part of an organ" is broader than the term "tubular", hence covers any organ containing fluids as for example the ventricular part of the heart.

In the present description, the term "pulsatory" means that each fiber or combination of fibers or gate or bundle is activated and deactivated in alternation with another fiber, or combination of fibers or gate or bundle in order to apply a pressure or not against the region of the hollow part around which the fiber has been placed, preferably so as to close or open said region of the hollow part. The frequency of alternate fiber, combination of fibers, gate or bundle activation is dependent upon the nature of the tissues and inside organ pressure, and is adjusted so that no tissue erosion and burn appear after several months of implantation.

In the present description, the term "contractile material" means in particular Electro Active Polymers (EAP), Electro Active Ceramics (EAC), Shape Memory Alloys (SMA). Any suitable material can be used for the fibers. A suitable SMA material for the contractible fibers is Nitinol™. In this case the fibers can be stretched by as much as 4% when below the transition temperature, and when heated, they contract, recovering thereby to their original, shorter length with a usable amount of force in the process. Temperature range varies according to the fiber's physical characteristic and is usually comprised between 37° C. to 70° C.

The fibers can have a spiral form in order to improve the length of the shortening.

Other particularly interesting materials are Biometal fibers (BMF) commercialized by Toki Corporation Inc., Japan (for example fibers BMX150 or BMF100). Those materials are able to reversibly contract upon a controlled heating caused by the supply of an electric current/voltage and can be repeatedly used several thousands of millions of times.

Such fibers are made for example of Ni—Ti—Cu alloy. For example, the composition ratios of Ni, Ti, and Cu are 46.9%, 44.8%, and 8.3%, respectively.

Advantageously, the fibers may be covered by an isolating substance to provide thermo-isolation of the structure thereby more reducing the risk of lesions of the surface of the organ to be contracted.

The support of the fibers may be rigid or flexible. It may be made part or whole of silicone or other elastomers.

In the apparatus of the invention, the artificial contractile structure is linked to a controller adapted to pulsatory and alternately contract the fibers and to a source of energy.

The controller and the source of energy can be implantable or placed outside the body of the patient. In a preferred embodiment, the controller and the source of energy are implantable. The controller and the source of energy can be integrated in the same device. Or the controller and the artificial structure can be integrated in the same device. In a preferred embodiment, the apparatus is a single device containing the artificial contractile structure, the implantable controller and the implantable source of energy.

In other embodiments, the controller can be implantable and the source of energy is placed outside the body of the patient. In other embodiments, both controller and source of energy are placed outside the body of the patient.

Preferably, the implantable source of energy is a transcutaneous rechargeable battery. Such battery is for example commercialized by GreatBatch.

The features of the battery depend on the application of the artificial structure, on the pressure to be applied, and on the number of fibers to contract.

The source of energy may also be an electro-active polymer designed to create energy by transformation of mechanical contraction, for example in the shape of an elastomeric band that is fixed on moving structures, such as beating heart, chest or bone joint. Such polymers have been described in many publications such as in the patent publications U.S. Pat. No. 7,233,097 and WO 2006/121818. The polymer may also be designed for an ultra-low power acoustic receiver, such as a light-weight piezoelectric polyvinylidene fluoride trifluoroethylene (PVDF-TrFE) copolymer cylindrical hydrophones (J Acoust Soc Am. 2008 May; 123(5):3013).

By selecting the length, the diameter and the shape of the fibers, the apparatus of the invention may be designed so that the required average power to supply by the source of energy is less than 3 W, preferably less than 1 W, more preferably less than 0.5 W and the maximum instantaneous power is less than 8 W, preferably less than 6 W. The maximum power can be supplied during 5 seconds only. The required voltage is dependent on the application. For example, the voltage may be less than 5 V for an urinary sphincter, and is preferably comprised between 4.5 V and 5 V. For a faecal sphincter, the voltage may be less than 20 V, and is preferably comprised between 17 V and 20 V.

Preferably, the structures or apparatus of the invention are operated in such a manner not to increase temperature of surrounding fluids or tissues by more than 3° C., preferably 2° C., more preferably 1° C., as it may be measured by any body-like fluids with a temperature probe that is placed for the temperature measurement at location where the induced heating is expected to be greatest, and preferably no more distant than 5 mm away from the device.

A specific test method is also described in the norm ASTM F2182-02a. Accordingly, the artificial sphincter is placed in a gel material phantom that simulates the electrical and thermal properties of the human body. The artificial sphincter is placed within the gel phantom with its receiving antenna below the gel surface. The control unit's external antenna for application of RF power and for transmitting of data is also positioned within the gel below the receiving antenna. The phantom material includes saline solution. Fiber optic temperature probes are placed for the temperature measurements at locations where the induced heating is expected to be greatest. The phantom is placed in the structures or apparatus of the invention with a cylindrical bore. An RF field should be applied with at least 1 W/kg averaged over the volume of the phantom. The temperature rise at the sensors is measured prior, during and after the RF application of approximately 15 minutes, or other appropriate period, depending on the mass and thermal conductivity of critical parts of the device. Temperature measurements at one or more locations away from the device serve as control.

The controller comprises a microprocessor that distributes current to fibers so that the fibers contract pulsatory and alternately, at the required pressure and at the required frequency.

The microprocessor is designed to generate micropulses having a duration lower than 100 ms, preferably comprised between 5 ms and 50 ms, more preferably between 10 ms and 20 ms and a power, which progressively increases, until the required length of the fiber is achieved. The duration between each pulse may be comprised between 5 ms and 50 ms, preferably between 5 and 10 ms. For example, the duration of the pulse may be 10 ms and the duration between each pulse may be 5 ms.

Moreover, the microprocessor may be designed to have a continuous feedback on the resistance of the fiber, which depends on the length of the fiber, in order to adapt the control according to the resistance of the fiber. Therefore, the apparatus of the invention is able to monitor itself, and can be used without sensor, which is a substantial advantage to further prevent tissue damages.

The microprocessor can be adjusted individually for each patient regarding pressure and frequency of opening and closing.

Ideally these adjustments can be done after implantation transcutaneously, preferably by a medicinal physician in order to optimize control of volume reduction (such as incontinence leaking).

The number of fibers, combination of fibers, gates or bundles to contract can be adapted to the required pressure to apply on the organ. For example, in the case of urinary sphincter, the number of gates to open and close can be adapted to the abdominal pressure.

The pressure of the activated fibers, combination of fibers, gate or bundle on the region of the organ to be contracted may be comprised between 10 g/cm$^2$ and 200 g/cm$^2$.

In a preferred embodiment, the apparatus of the invention comprises:
  i) an artificial contractile structure implantable into the human body and comprising one or more fibers being made of a contractile material, such as the contractile structures described above,
  ii) an implantable activator which upon activation will induce a reduction of a fibers length, such as the activator described above, wherein the activated fibers are designed to apply a pressure on an organ to be contracted, which is comprised between 10 g/cm$^2$ and 200 g/cm$^2$, during a period comprised between 30 seconds to 30 minutes, preferably between 30 seconds to 10 minutes, and more preferably between 1 minute to 5 minutes.

Each fiber, combination of fibers, gate or bundle, is preferably activated or deactivated several times a day, and most preferably several times an hour. The fiber, combination of fibers, gate or bundle may be activated during a period comprised between 30 seconds to 30 minutes, preferably between 30 seconds to 10 minutes, and more preferably between 1 minute to 5 minutes. The relaxation time is dependent on the number of regions which are to be contracted by the fibers, combinations of fibers, gates or bundles.

For example, if the structure is adapted to contract four regions of an organ, and if only one fiber, combination of fibers, gate or bundle is activated at the same time, each fiber, combination of fibers, gate or bundle, can be activated during one minute and deactivated during three minutes in an alternating manner. In another embodiment, each fiber, combination of fibers, gate or bundle can be activated during five minutes and deactivated during fifteen minutes in an alternating manner. If the structure is adapted to contract three regions of an organ, each fiber, combination of fibers, gate or bundle, can be activated during one minute and deactivated during two minutes in an alternating manner.

The activation of each fiber, combination of fibers, gate or bundle can be random or sequential.

Only one or several fibers, combinations of fibers, gates or bundles can be contracted at the same time. In other embodiments, one fiber, combination of fibers, gate or bundle can remain contracted or closed whereas another fiber, combination of fibers, gate or bundle is contracted or closed.

All these embodiments are obtained by means of an adequate controller. Said controller is designed to allow an adjustment of the pressure of the contractile structure on the organ according to the patient's need, by adjusting the voltage of the current distributed to the fibers. Advantage is that the physician can customize the optimal pressure of the contractile structure to side effects on the organs, for example by means of a magnet placed around the apparatus. The parameters of the controller can be adjusted by the physician after the implantation of the apparatus during the postoperative consultations.

The control of the contractile structure, and more especially its opening can be achieved by a manual control of the controller by means of a remote control or by means of a switch placed under the skin, which is activated by pressure on one or several buttons. Preferably, the switch comprises several buttons and the sequence for pressing the buttons is predetermined in order to avoid accidental opening of the structure.

In a preferred embodiment, the apparatus of the invention comprises:
i) an artificial contractile structure implantable into the human body and comprising one or more fibers being made of a contractile material, such as the contractile structures described above,
ii) an implantable electric activator which upon activation will induce a reduction of a fibers length, such as the activator described above, wherein the average power to supply by the activator is less than 3 W, preferably less than 1 W, more preferably less than 0.5 W.

The artificial contractile structure may be a structure comprising any separate elements described above, or any appropriate contractile structure known by one skilled in the art.

The activator or controller may be a controller having any separate features described above, or any appropriate controller known by one skilled in the art.

In another embodiment, the artificial structure is made for urinary incontinence and is optimally designed for female anatomy. Such a structure is very small and minimally invasive. In such structure, the support has a concave shape adapted to the form of the upper part of the vagina. The support is preferably soft and can be made of silicone. The structure, placed around the urethra to be contracted, lies on the upper part of the vagina and allows to avoid any trouble for the patient. Preferably, the three dimensions of such a structure do not exceed 10 mm. The possible dimensions of such structure are for example 10×8×8 mm.

Example 1

Referring to FIGS. 1 to 4, one embodiment of an artificial contractile structure 1, used to treat urinary incontinence, comprises a rigid support 2 having the form of a clamp formed of two parts jointed by a hinge 3. The clamp is adapted to be placed around the tubular part of an organ to be contracted, for example the urethra. Each part comprises teeth 4, distributed along the support 2 to form four pairs of teeth 4a and 4b. For each pair of teeth 4a, 4b, a fiber 5 made of shape memory material is fixed to the inside of the teeth 4a, 4b in order to cross the area delimited by the associated teeth 4a and 4b. Therefore, each fiber 5 and its corresponding pair of teeth 4 allow forming four gates, each being able to constrict one region of the tubular part to close it, in a pulsating and alternating manner, and independently of each other.

Figure 2:
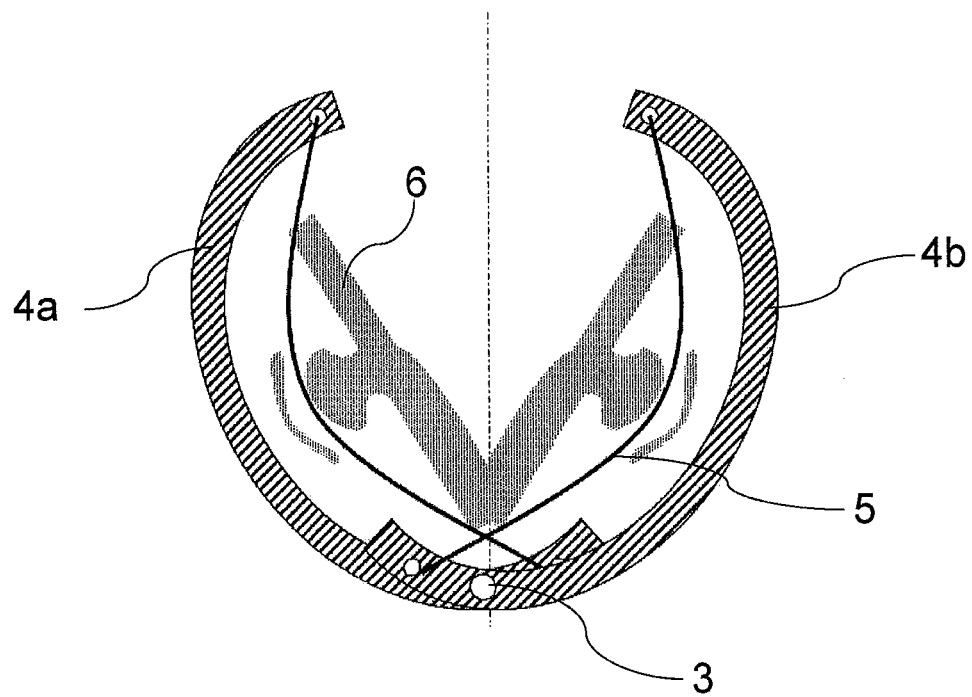
FIG. 2 is a cross-sectional view of structure of FIG. 1, in open position.

As shown by FIG. 2, each end of the fiber 5 is fixed to each tip of tooth 4a, 4b and the fiber is crossed at the bottom of the support 2. The fibers 5 are adapted to be non-rectilinear in the rest position, and to have a reduced length in the activated position. The length of the fiber is chosen so that the pressure of each fiber, when it is contracted, on the tubular part, is high enough to completely close the tubular part.

A protecting element 6 is disposed inside the clamp, above the fibers 5, in order to protect the tissue from the heating of the fibers 5 and to better distribute the pressure of the fibers to the tubular part of the organ. Such protecting element 6 can be made of silicone.

In the apparatus of the invention, the structure 1 is used with an activator or controller comprising a microprocessor adapted to distribute current to fibers 5 by conducting wires 8 and to drive the contraction of the fibers in order to pulsatory and alternately contract said fibers. There are also means for opening on demand said artificial contractile structure, used by the patient to inactivate all the fibers of the structure and open all the gates of the structure, and an implantable source of energy, for example a rechargeable battery. A percutaneous energy transfer supply can be developed for battery recharge. The apparatus can further comprise sensing means selected from pressure, temperature and movement sensing means. Such sensing means can to be fixed to the support of the artificial contractile structure.

Figure 3:
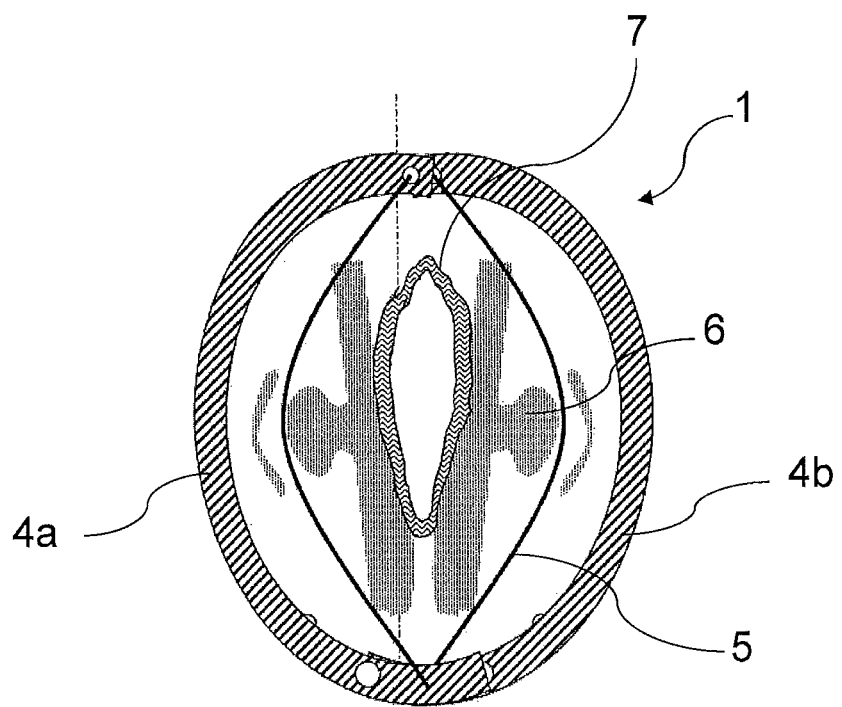
FIG. 3 is a cross-sectional view of structure of FIG. 1, in closed position around a tubular organ, the fibers being inactivated.
Figure 4:
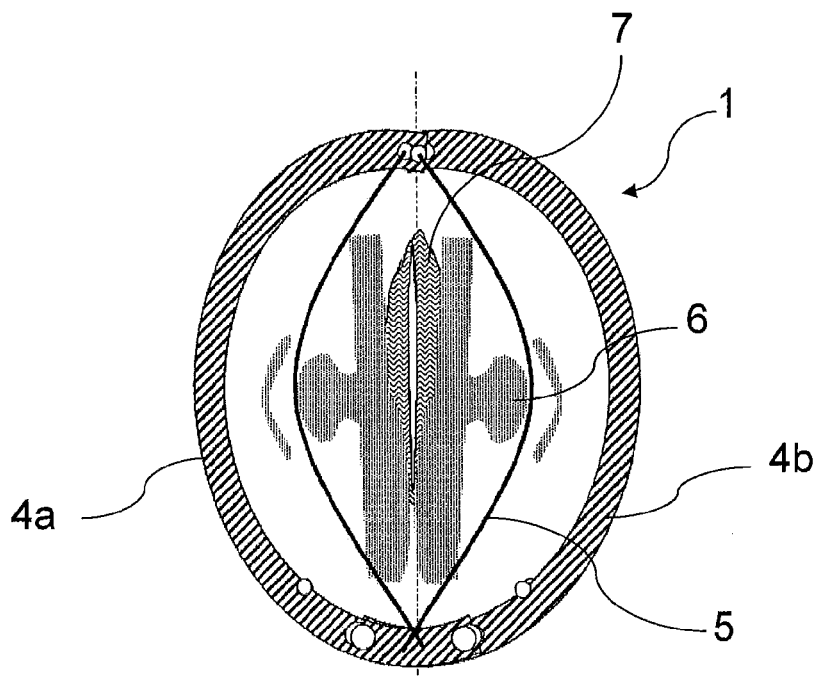
FIG. 4 is a cross-sectional view of structure of FIG. 1, in closed position around a tubular organ, the fibers being activated.

Referring to FIGS. 3 and 4, the structure 1 is placed and fixed around an organ to close 7 and the clamp is closed. The fibers 5 are therefore distributed along the organ 7. In inactivated position, as shown by FIG. 3, one fiber 5 is in rest position and is not contracted. The region of the organ 7 around which the fiber 5 has been placed is not compressed and then not closed.

When an electric current/voltage is applied to the fiber 5 by the controller, the fiber 5 is activated and contracts, as shown by FIG. 4, in such a way as to reduce its length and then to reduce the diameter of the region of the organ 7 around which the fiber 5 has been placed, until to close said region of the organ 7. More precisely the fiber movement occurs in a plane which is transverse with respect to the direction of the tubular organ 7.

As there are at least two pairs of teeth, there are at least two gates formed by the teeth. The fiber of each gate is independently, pulsatory and alternately activated in order to contract one or the other region around which the fiber has been placed, in a pulsating and alternating manner. This allows an alternate contraction along said tubular part, several times an hour. Such a configuration avoids necrosis of the underlying tissue.

The controller or activator is designed to activate at least one fiber so that at least one region of the tubular part is closed to avoid incontinence. The patient deactivates the apparatus if necessary, so that each fiber is inactivated to open each region of the tubular part of the organ, allowing the passage of the urine, for example.

Moreover, if the apparatus of the invention fails, there is no current in the fibers, which are therefore in the rest position. The structure 1 remains open. No surgery is necessary to allow the passage of the urine, for example.

Figure 5:
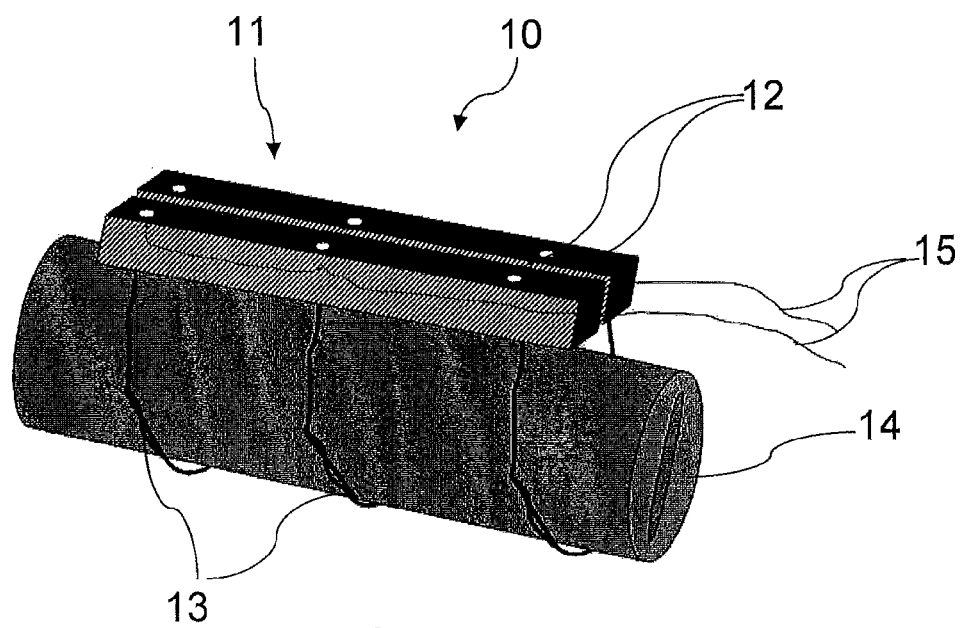
FIG. 5 is a side view of another embodiment of the structure according to the present invention, in closed position around a tubular organ, the fibers being activated.

Referring now to FIG. 5, another embodiment of the artificial contractile structure 10 comprises a support 11 comprising two parallel rods 12 to which three fibers 13 made of shape memory material are fixed by their ends. Each end of a fiber 13 is fixed to each rod 12 so that each fiber 13 forms a loop adapted to be placed around the tubular part 14 of an organ. The loops form three gates, each gate being able to constrict one of the three regions of the tubular part 14 to close it. As described above, each fiber 13 is linked to an activator or a controller by conducting wires 15, said activator driving the contraction of the fibers 13 in order to pulsatory and alternately contract them, so that each region of the tubular part is completely closed, in a pulsating and alternating manner, independently of each other.

Figure 6:
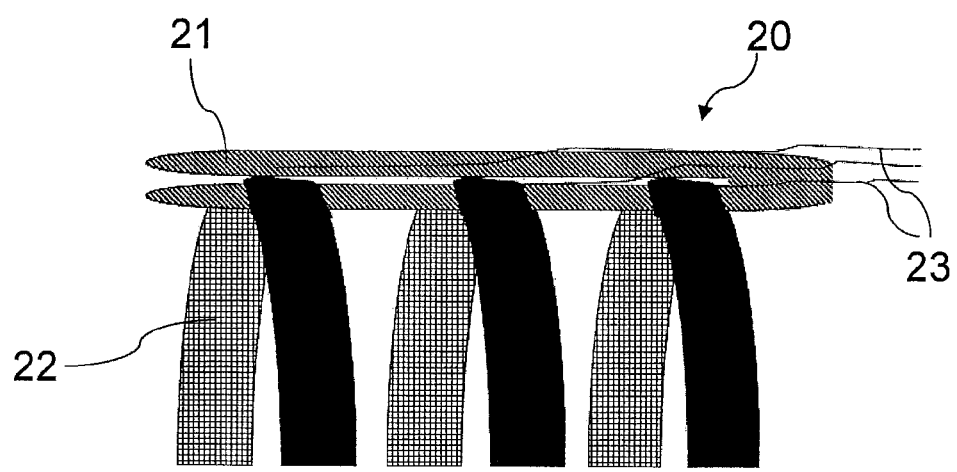
FIG. 6 represents another embodiment of the structure according to the present invention.

Referring now to FIG. 6, another embodiment of the artificial contractile structure 20 comprises a rod 21 in U shape. Three strips 22 are fixed by their central part to the first leg of the U rod 21. Each leg of the U rod carries the current necessary to activate the strips. Preferably, such strips 22 are made of electroactive polymer, for example a ionic polymer-metal composite (IPMC). The second leg of the U rod 21 allows clamping the strips 22 and the electric current to be applied to one side of the strips 22.

Each strip 22 forms a U adapted to be placed around the tubular part of an organ, the U fibers forming three gates, each gate being able to constrict one region of the tubular part to close it, in a pulsating and alternating manner. The strips 22 and the second leg of the U rod 21 are linked to an activator or controller by conducting wires 23. As describes above, said activator or controller is suitable to drive the contraction of the strips 22 in order to pulsatory and alternately contract them, so that each region of the tubular part is completely closed, in a pulsating and alternating manner, independently of each other.

Figure 7:
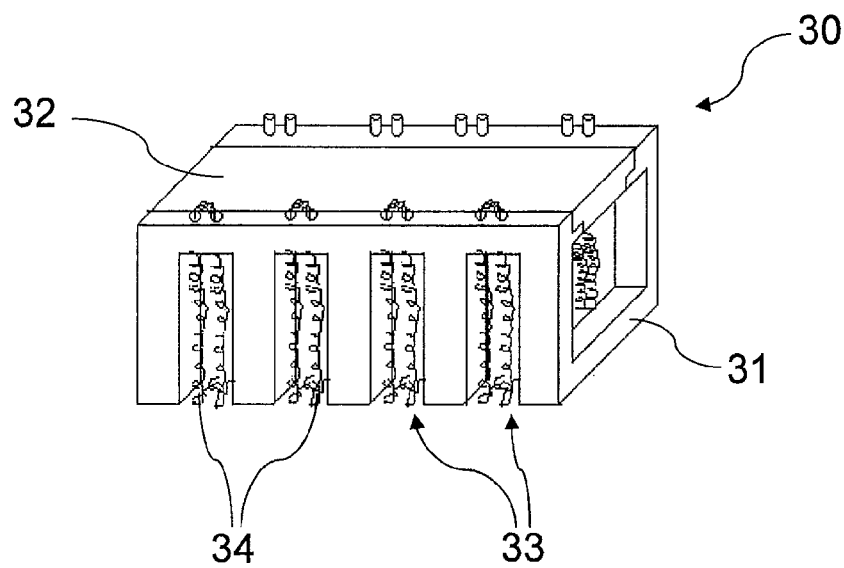
FIG. 7 is a side view of another embodiment of the artificial structure according to the present invention.
Figure 8:
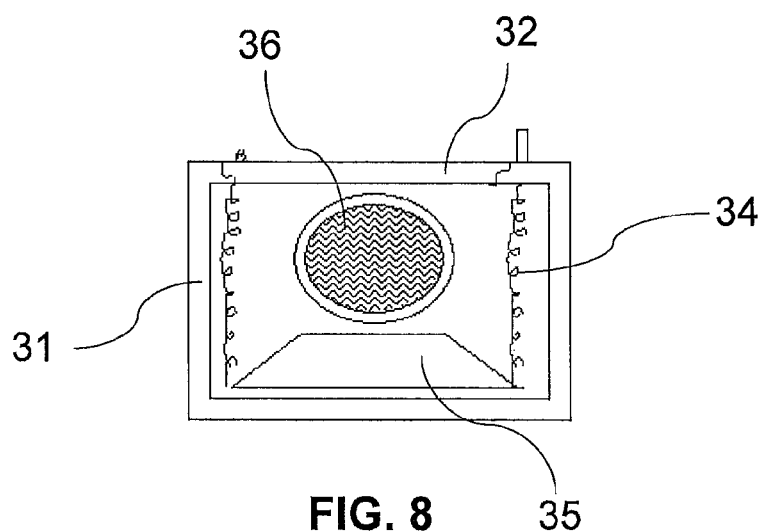
FIG. 8 is a cross-sectional view of structure of FIG. 7, in closed position around a tubular organ, the fibers being inactivated.
Figure 9:
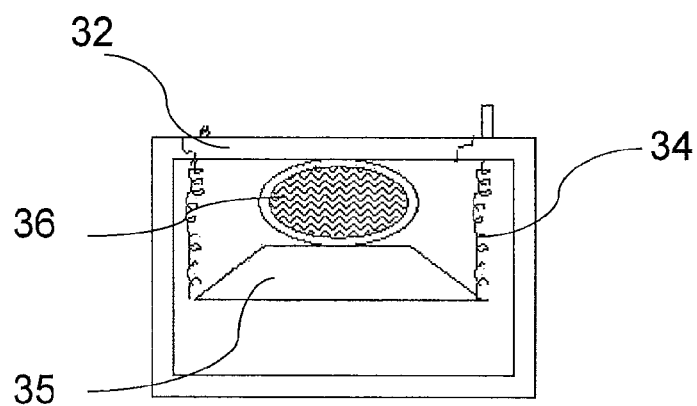
FIG. 9 is a cross-sectional view of structure of FIG. 7, in closed position around a tubular organ, the fibers being activated.

Referring now to FIGS. 7 to 9, another embodiment of the artificial contractile structure 30 comprises a housing 31 adapted to be placed around the tubular part 36 of an organ. The housing 31 is closed by a sliding cover 32. The walls of the housing 31 comprise four openings 33 in which fibers 34 have been inserted. The fibers 34 are suspended by their ends to the upper wall of the housing 31. The central part of each fiber 34 comprises a press pad 35, placed opposite the sliding cover 32. In order to reduce the consumption of energy, the fibers 34 have a spiral form on each side of the press pad 35, and are straight when they are under the press pad 35.

In inactivated position, as shown by FIG. 8, one fiber 34 is in rest position and is not contracted. The region of the organ 36 around which the fiber 34 has been placed is not compressed by the press pad 35 and then not closed.

When an electric current/voltage is applied to the fiber 34 by the activator or controller, the fiber 34 is activated and contracts, as shown by FIG. 9, in such a way as to reduce its length and then to lift the press pad 35. The tubular part 36 is then compressed between the press pad 35 and the sliding cover 32 until to be completely closed.

As explained above, the fibers 34 and their press pads 35 form four gates, each gate being able to constrict one region of the tubular part 36 to close it, in a pulsating and alternating manner, in such a way as to avoid necrosis of the underlying tissue.

Such artificial structure, comprising four gates alternatively activated, was tested with a conduit, similar to a urethra, to measure the leak, the latency and the spotting. The leak is defined as the flow through the conduit when the artificial structure is on. The latency is defined as the time between the release of gate activation and the beginning of flow through conduit. The spotting is defined as the volume of liquid passed through the conduit during the sequential activation of four gates. The results are shown in Table I below:

TABLE I

| Leak | Pressure in the bladder 120 cm $H_2O$ | 0 |
|---|---|---|
| Latency | Pressure in the bladder <100 cm $H_2O$ | 1.5 second |
| Spotting | Pressure in the bladder <100 cm $H_2O$ | 0 |

These results show the high efficiency of the artificial structure of the invention.

Figure 10:
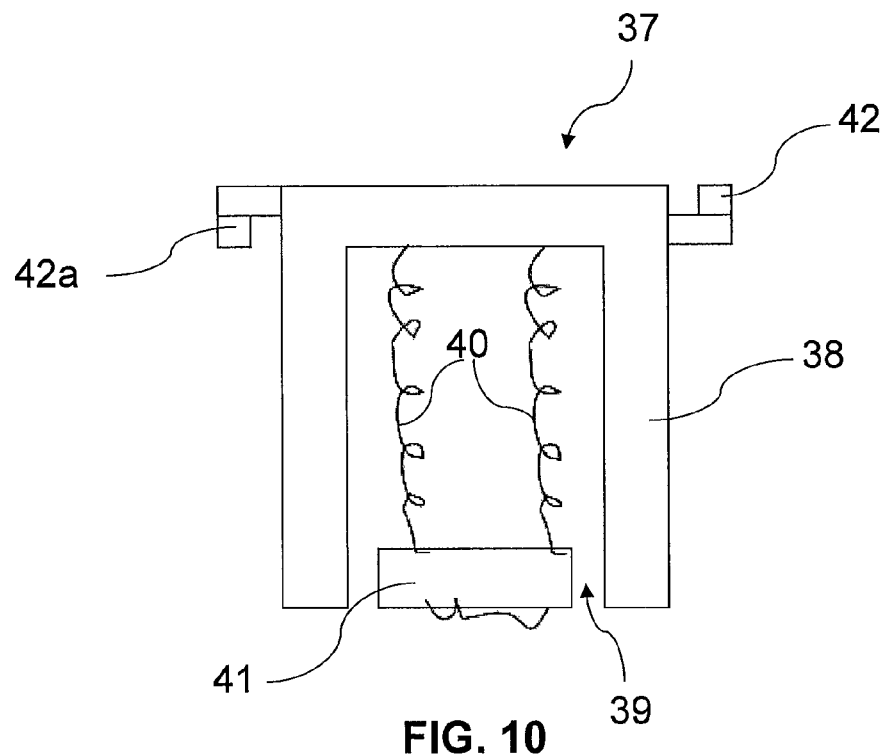
FIGS. 10 and 11 are side views of another embodiment of the artificial structure according to the present invention, derived from the embodiment of FIGS. 7 to 9.
Figure 11:
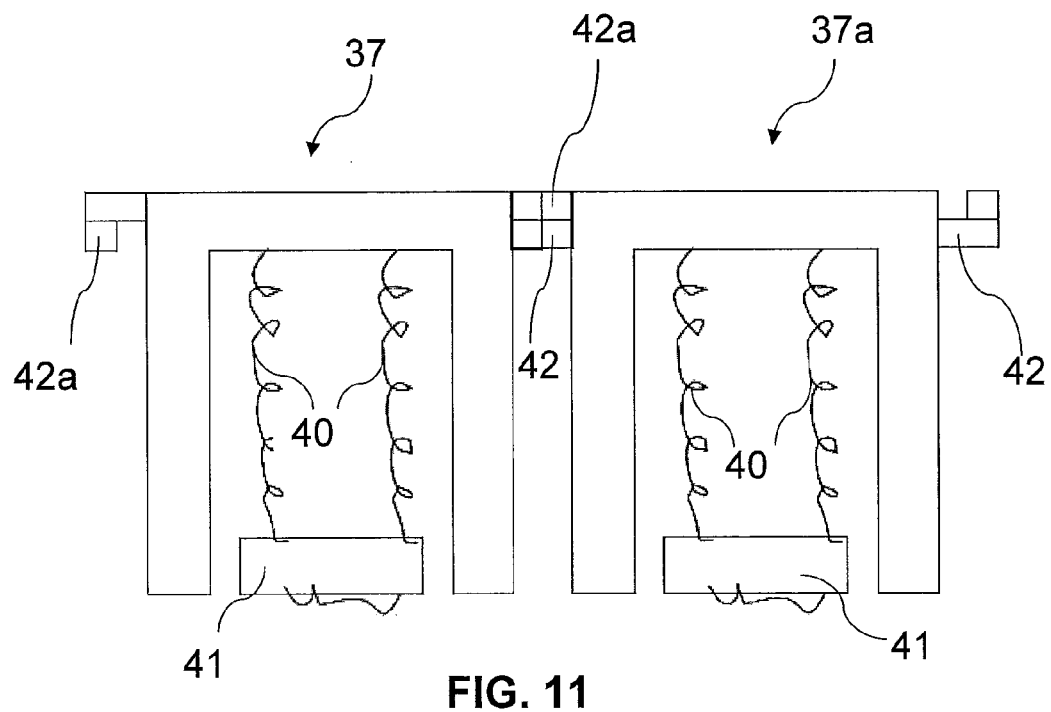

Referring now to FIGS. 10 and 11, in another embodiment, the artificial contractile structure 30 is divided in several elements 37, each corresponding to one of the gates. Each element 37 comprises a support defining a housing 38, similar to the housing 31, and adapted to be placed around the tubular part of an organ. The walls of the housing 38 comprise one opening 39 in which fibers 40 have been inserted. The fibers 40 are suspended by their ends to the upper wall of the housing 38. The central part of each fiber 40 comprises a press pad 41. Such fibers 40 and press pad 41 works like the fibers 34 and press pad 35. Moreover, each side of the housing 38 comprises a hook 42, 42a designed to cooperate with a complementary hook of another element 37, as shown in FIG. 11, in order to allow the assembly to another element 37a, identical or similar to the element 37, to form the artificial contractile structure. The elements 37 and 37a are connected to the controller so that their fibers 40 contract alternatively, as described above. Such embodiment allows obtaining a modular contractile structure. Other elements 37 can be added to obtain the appropriate length of the structure.

Obviously, the elements 37 and 37a can be also assembled by interlocking, sewing, sticking. The elements 37 and 37a can be also juxtaposed one against the over. This embodiment allows increasing the flexibility of the contractile structure.

Figure 12:
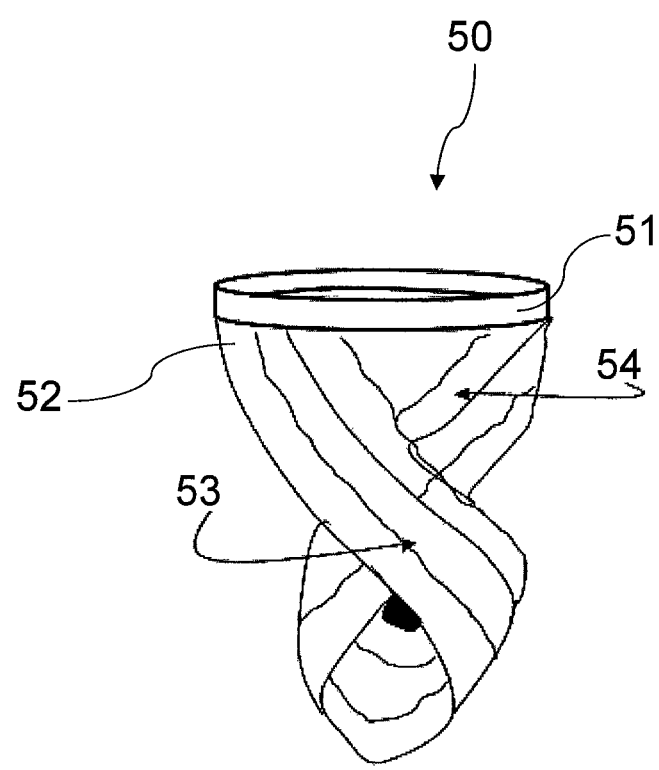
FIG. 12 is a front view of another embodiment of the artificial structure according to the present invention.

Referring now to FIG. 12, it is shown another embodiment of the artificial contractile structure, designed for assisting ventricular contraction. The structure 50 comprises a support ring 51 and three contractile bundles of fibers 52, 53 and 54, designed for being placed around the ventricular part of the heart. Each bundle 52, 53 and 54 is suspended by its ends to the ring 51 so as to form a loop, which will be placed around the ventricular part of the heart. When an electric current/voltage is applied to the fibers of each bundle by the controller, the fibers are activated and contract, in such a way as to reduce the volume of the heart in the corresponding different regions of the heart and to assist ventricular contraction. Each bundle is linked to the controller so as to contract the corresponding region of the heart, in a pulsating and alternating manner relating to the other bundles.

Example 2

An animal study has been designed to assess mechanical effects of a contractile apparatus placed in on the heart atrium to function as a pump. This apparatus, also called Atripump, is made of a dome shape silicone coated nitinol actuator 5×45 mm. The dome is sutured on the external surface of the right atrium (RA). A pacemaker like control unit drives the dome and the dome provides the mechanical support to the blood circulation.

In 5 adult sheeps of 65±4 Kg, under general anaesthesia, the right atrium was surgically exposed and the dome sutured onto the epicardium. Atrial Fibrillation (AF) was induced using rapid epicardial pacing (600 beats/min, Biotronik, Germany). Swan-Ganz catheter was inserted in the left jugular vein to measure the central venous pressure and pulmonary pressure. Computation of the ejection fraction (EF) of the right atrium was obtained with intracardiac ultrasound (ICUS) inserted in the right jugular vein. Right atrium EF was calculated in baseline, AF and Atripump assisted AF conditions. Major hemodynamic parameters, histology and dome temperature were acquired as well.

Dome's contraction rate was 60/min with power supply of 12V, 400 mA for 200 ms and run for 2 consecutive hours. Mean temperature on the right atrium surface was about 39° C. for 3 sheeps, and higher for the other sheeps.

After on month implant experimentation, the histology analysis showed the absence of any necrosis on the atrium for the sheeps having the Atripump that is providing a mean temperature on the right atrium surface of about 39° C., while necrosis appeared when temperature on the right atrium surface was higher than 40° C.

The invention claimed is:

1. An artificial contractile device, comprising:
   a structure adapted to be placed around a hollow part of an organ to be contracted, the structure comprising at least two gates,
   each one of said gates configured to operatively contract a corresponding region of said hollow part, each region being separate and distinct from any other region, each of said gates further configured to apply pressure on the corresponding region of the hollow part independently of any other of said gates, said at least two gates, in operation, contracting alternately with respect to each other to alternately apply pressure to each of said regions during a period comprised between 30 seconds to 30 minutes in a manner such that said operative contracting does not raise a temperature of fluids or tissues surrounding the hollow part above 40° C.

2. The artificial contractile device according to claim 1, wherein the at least two gates comprise a hinged clamp configured to be placed around the hollow part, the hinged clamp forming at least two pairs of teeth, and
   wherein each of said gates is configured to independently constrict a unique and corresponding region of a urethra in a pulsating and alternating manner in order to close the hollow part.

3. The artificial contractile device according to claim 1, wherein the at least two gates comprise a U rod.

4. The artificial contractile device according to claim 1, further comprising:
   an activator linked to said device and adapted to pulsatory and alternately contract the gates of the structure, said activator being configured such that the temperature of the fluids or tissues surrounding the hollow part are not raised above 40° C.

5. The artificial contractile device according to claim 4, wherein said activator is configured not to raise the temperature of the fluids or tissues surrounding the hollow part above 39° C.

6. The artificial contractile device according to claim 4, wherein said activator is configured not to raise the temperature of the fluids or tissues surrounding the hollow part above 38° C.

7. The artificial contractile device according to claim 4, wherein the activator and the structure are configured to apply, in a pulsating and alternating manner, a pressure on the hollow part of the organ between 10 g/cm$^2$ and 200 g/cm$^2$.

8. The artificial contractile device according to claim 1, wherein the period is between 30 seconds to 10 minutes.

9. The artificial contractile device according to claim 8, wherein the period is between 1 minute to 5 minutes.

10. The artificial contractile device according to claim 1, wherein the structure comprises a support and one or more fibers fixed to said support,
    said fibers being made of a contractile material activatable by an activator configured to maintain said structure in either of a rest position and an activated position, the fibers being of shorter length in the activated position than when in the rest position, and the fibers being distributed along said support in order to reduce a volume of the hollow part when said fibers are contracted in said activated position.

11. The artificial contractile device according to claim 10, wherein the fibers have a diameter and shape such that the activator requires less than 3 W in operation to place the fibers from the rest position to the activated position.

12. The artificial contractile device according to claim 10, wherein the fibers have a diameter and shape such that the activator requires less than ½ W in operation to place the fibers from the rest position to the activated position.

13. The artificial contractile device according to claim 10, wherein the fibers have a diameter and shape such that the activator requires less than ½ W in operation to place the fibers from the rest position to the activated position.

14. The artificial contractile device according to claim 10, wherein the activator comprises a microprocessor configured to generate micropulses having a duration less than 100 ms and a power, which progressively increases, until a required length of the fibers is achieved.

15. The artificial contractile device according to claim 14, wherein the micropulses have a duration between 10 ms and 20 ms.

16. The artificial contractile device according to claim 14, wherein the micropulses have a duration between 5 ms and 50 ms.

17. The artificial contractile device according to claim 10,
    wherein the fibers are distributed along said support in order to be able to reduce the volume of the hollow part, when said fibers are contracted in at least two distinct regions of the hollow part, and
    wherein the fibers are configured to be activated pulsatory and alternately.

18. The artificial contractile device according to claim 17,
    wherein said structure is configured to be placed around a tubular part of the organ to be contracted,
    wherein the fibers are distributed along the support in such a way that they are capable of reducing a diameter of said tubular part, when said fibers are contracted, in at least two distinct regions of the tubular part, and
    wherein the fibers are configured to be activated pulsatory and alternately.

19. The artificial contractile device according to claim 10, wherein a transition from the rest position towards the activated position or vice-versa is defined by a fiber movement along a lateral direction perpendicular with respect to a fiber length.

20. The artificial contractile device according to claim 10, wherein the fibers are fixed on a support that covers at least 20% of a surface of the hollow part where the structure is placed with at least two fibers forming a loop on the hollow part and connected to the support.

21. The artificial contractile device according to claim 20, wherein the fibers are fixed on a support that covers 50% of said surface.

22. The artificial contractile device according to claim 10,
wherein the support is formed as a hinged clamp configured to be placed around the hollow part, the hinged clamp comprising at least two pairs of teeth, and
wherein one or more fibers are fixed to an inside of each pair of teeth in order to cross an area delimited by the teeth so as to form said at least two gates.

23. The artificial contractile device according to claim 10, wherein the support comprises parallel rods to which at least two fibers are fixed by their ends, so that each fiber forms a loop configured to be placed around the hollow part, the loops forming said at least two gates.

24. The artificial contractile device according to claim 10, wherein the support comprises a U rod to which at least two fibers are fixed by their central part, so that each fiber forms a U adapted to be placed around the hollow part, the U fibers forming said at least two gates.

25. The artificial contractile device according to claim 10,
wherein the support comprises a housing adapted to be placed around the hollow part, said housing configured to be closed by a sliding element, and
wherein at least two fibers are suspended by their ends to the support, the central part of each fiber comprising a press pad placed opposite the sliding element, the fibers and their press pads forming said at least two gates.

26. The artificial contractile device according to claim 10,
wherein the support is divided in separable individual elements, each of said individual elements comprising fibers distributed along said individual element for reducing the volume of the hollow part when said fibers are contracted in operation, and
wherein the fibers of each of said individual elements are configured to be contracted independently of any other of said individual elements.

27. The artificial contractile device according to claim 26, wherein each of said individual elements comprises assembly means for cooperating with complementary assembly means of another of said individual elements.

28. The artificial contractile device according to claim 10,
wherein the support has a form configured to be placed around the hollow part to be contracted, and
wherein the fibers are configured to form at least two bundles, each bundle being suspended by their ends to the support and forming a loop around said hollow part, each bundle being configured to contract one unique region of the hollow part in a pulsating and alternating manner.

29. The artificial contractile device according to claim 1, wherein the structure is configured to be placed around one of i) a urethra, and ii) a ventricular part of a heart.

30. A method of assisting or replacing a natural sphincter, comprising:
placing an artificial contractile structure around a hollow part of an organ to be contracted, said artificial contractile structure comprising at least two gates,
each one of said gates being configured to operatively contract a corresponding region of said hollow part, each region being separate and distinct from any other region, and each of said gates further configured to apply pressure on the corresponding region of the hollow part independently of any other of said gates; and
applying pressure to said regions by contracting said gates in a manner alternating among each gate for a period comprised between 30 seconds to 30 minutes, said contracting not raising a temperature of either of fluids or tissues surrounding the hollow part above 40° C.

31. A method of assisting or replacing a paralyzed muscle, comprising:
placing an artificial contractile structure around a hollow part of an organ to be contracted, said artificial contractile structure comprising at least two gates,
each one of said gates being configured to operatively contract a corresponding region of said hollow part, each region being separate and distinct from any other region, and each of said gates further configured to apply pressure on the corresponding region of the hollow part independently of any other of said gates; and
applying pressure to said regions by contracting said gates in a manner alternating among each gate for a period comprised between 30 seconds to 30 minutes, said contracting not raising a temperature of either of fluids or tissues surrounding the hollow part above 40° C.

32. The method according to claim 30, wherein the contracting does not raise the temperature of the fluids or the tissues surrounding the hollow part above 39° C.

33. The method according to claim 30, wherein the contracting does not raise the temperature of the fluids or the tissues surrounding the hollow part above 38° C.

34. The method according to claim 31, wherein the contracting does not raise the temperature of the fluids or the tissues surrounding the hollow part above 39° C.

35. The method according to claim 31, wherein the contracting does not raise the temperature of the fluids or the tissues surrounding the hollow part above 39° C.

36. The artificial contractile device according to claim 1, wherein the structure comprises at least three of said gates.

* * * * *

UNITED STATES PATENT AND TRADEMARK OFFICE
CERTIFICATE OF CORRECTION

PATENT NO.       : 8,439,979 B2                                              Page 1 of 1
APPLICATION NO. : 12/667645
DATED            : May 14, 2013
INVENTOR(S)      : Tozzi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 315 days.

Signed and Sealed this
Eighth Day of September, 2015

Michelle K. Lee
*Director of the United States Patent and Trademark Office*